(12) United States Patent
Teslenko et al.

(10) Patent No.: US 6,333,399 B1
(45) Date of Patent: Dec. 25, 2001

(54) PROCESS FOR PRODUCING CHITOSAN-GLUCAN COMPLEXES, COMPOUNDS PRODUCIBLE THEREFROM AND THEIR USE

(75) Inventors: Alexander Teslenko, Eduard-Morike-Strasse 4a, D-52249 Eschweiler (DE); Woewodina Irina Nikolaewna, Julich (DE)

(73) Assignee: Alexander Teslenko, Hagen (DE)

( * ) Notice: Subject to any disclaimer, the term of this patent is extended or adjusted under 35 U.S.C. 154(b) by 0 days.

(21) Appl. No.: 08/894,142

(22) PCT Filed: Feb. 12, 1996

(86) PCT No.: PCT/EP96/00590

§ 371 Date: Oct. 27, 1997

§ 102(e) Date: Oct. 27, 1997

(87) PCT Pub. No.: WO96/25437

PCT Pub. Date: Aug. 22, 1996

(30) Foreign Application Priority Data

Feb. 13, 1995 (DE) .............................. 195 04 640

(51) Int. Cl.$^7$ .......................... C08B 37/08; C07H 15/00; C07H 1/00; C07H 3/00
(52) U.S. Cl. .......................... 536/20; 536/17.2; 536/101; 536/127; 536/128; 536/123; 536/123.12; 536/123.1; 435/101; 424/184.1; 424/185.1
(58) Field of Search ................................ 424/184.1, 180; 536/20, 17.2, 101, 127, 128, 123, 123.1, 123.12; 435/101

(56) References Cited

U.S. PATENT DOCUMENTS

| 4,282,351 | * | 8/1981 | Muzzarelli . |
| 4,368,322 | * | 1/1983 | Muzzarelli . |
| 4,806,474 | * | 2/1989 | Hershberger . |
| 5,488,040 | * | 1/1996 | Jamas et al. . |
| 5,747,475 | * | 5/1998 | Nordquist et al. . |

FOREIGN PATENT DOCUMENTS

| 2026516 | 2/1980 | (GB) . |
| 2259709 | 3/1993 | (GB) . |
| 9014071 | 11/1990 | (WO) . |

OTHER PUBLICATIONS

Database WPI, Week 9622, Derwent Publications Ltd., London, GB; XP002005551, Sep. 20, 1995.

* cited by examiner

*Primary Examiner*—Nita Minnifield
(74) *Attorney, Agent, or Firm*—Jacobson Holman, PLLC

(57) ABSTRACT

A process for the preparation of chitosan-glucan complexes from biological sources by treating said biological sources with solutions, characterized in that a) chitin-containing microorganisms as said biological sources are treated at least once with a first alkaline solution;

b) thereafter, the product obtained from step a) is treated with diluted mineral acid;

c) followed by a further treatment with a second alkaline solution the alkalinity of which is higher than that of the alkaline solution of step a) to incomplete deacetylation of the fraction obtained step b);

d) separating the solid components, discarding the supernatant, neutralizing and washing the residue with water.

21 Claims, No Drawings

PROCESS FOR PRODUCING CHITOSAN-GLUCAN COMPLEXES, COMPOUNDS PRODUCIBLE THEREFROM AND THEIR USE

This is a 371 of PCT/EP96/00590, filed Feb. 12, 1996.

The present invention pertains to a process for the preparation of chitosan-glucan complexes from biological sources, a material essentially consisting of a chitosan-glucan complex obtainable by the process according to the invention, materials shaped therefrom, a wound healing means, and uses of the materials according to the invention.

Cell walls of microorganisms containing chitin have already been used for many applications in the prior art. Thus, it is possible to bind and accumulate metal ions from water by means of microorganisms. The sorptive power of the microorganisms is attributed to the cell walls. Especially cell walls of microscopic fungi, actinomycetes and yeasts contain various complexes of polysaccharides. Thus, for instance, the inner layer of the cell wall of *Neurospora crassa*, Penicillium sp., Aspergillus sp. consists of chitin microfibers incorporated in a 1,3-polyglucan-matrix. The cell walls form a barrier against deleterious environmental influences and possess a protective function for the corresponding microorganisms. Thus, the chitin content in fungi can reach up to 45% of the cell components (e.g. in *Penicillium digitatum*). An important aminopolysaccharid, chitosan, can be obtained from chitin. The primary amino groups of chitosan or its complexes can selectively form particular bonds with metal ions. Chitosan has been used as a sorbent in the heavy metal elimination and as a flocculant for negatively charged colloids. In addition, polymers based on chitin are known to be capable of causing a decrease in cholesterol content. Chitosan could achieve much importance for the application on many technical fields. To date, however, no satisfactory process has been provided for obtaining chitosan derivatives which may be employed, for example, in medicine, food industry or environmental and disposal engineering. Thus, to date, the mycelium, for example, from *Rhizopus arhisus*, has been treated with 4% sodium dodecylsulfate solution, which is an aggressive detergent, mechanically disrupted, centrifuged and washed with water. However, a total disruption of the native cell wall structure is unavoidable thereby. This has a negative effect on sorptivity. In addition, it has been known to process cells, for instance, from *Saccharomyces cerevisiae*, with denaturing agents, such as 8 M urea solution, 1 M aqueous potassium hydroxide and 33 mM acetic acid solution. This yields substances having a low sorption capacity for heavy metal ions. These methods are described in Biotechnol. & Bioeng., Vol. 24, N2, p. 385–401, 1982, The Mechanism of Uranium Biosorption by Rhizopus arhisus, The Fungi, Eds. Ainsworth G. C., Sussman, A. V., Academic Press 1965, p. 46–76, and in GB-2,188,135 A1. GB-2,102,506 pertains to the recovery of chitin-containing materials from the molds Mucor mucedo and *Risomucor miecheli*. This involves incubation with 8% $H_2O_2$ solution at 100° C. for one hour followed by treatment with sodium silicate solution. A material is obtained which has high protein and ash contents. This may have an adverse effect on the flexibility of the corresponding materials. The recovery of chitin-containing materials for use in wound healing is described in U.S. Pat. No. 3,632,575. This involves first extraction with chloroform, treatment with 1.0 N aqueous sodium hydroxide at room temperature for 18 hours, followed by the addition of low-concentrated hydrochloric acid and dialysis with distilled water. Said chloroform extraction is a problematic step in industrial scale since the use of large amounts of chloroform is not recommendable for ecological and industrial hygiene reasons.

DE 29 23 802 A1 pertains to a process for treating mycelia of the mold *Mucor rouxii* with 40% aqueous sodium hydroxide at 128° C. for four hours. In a similar way, mycelia of *Aspergillus niger*, for example, are treated with 40% aqueous sodium hydroxide for six hours. A chitosan-glucan complex is obtained in an amount of from 32 to 52% of the total weight of the fungal mycelia, the chitosan-glucan complex obtained being capable of binding heavy metal ions, e.g., copper. However, this process has an advantage in that it is impossible to ensure the required degree of purity with respect to proteins, lipids and carbonates in this complex. A high carbonate content has also an adverse effect on the flexibility and applicability of the materials obtained. In addition, it is a drawback that the native structure of the mold cell walls is completely disrupted, and that control of the degree of deacetylation of the chitin is not possible, either.

It has been the object of the invention to provide a process which, in the first place, generally avoids the disadvantages of the prior art, i.e. is capable, in particular, of processing the fungal mycelia in such a way that as extensive as possible a use thereof in different technical fields becomes possible, and, in particular, of controlling the degree of deacetylation. In addition, the process is to be environmentally safe and still ecological.

The object of the invention is surprisingly achieved by a process according to the features and to preferred embodiments in the following description of the process according to the invention.

The process according to the invention for the preparation of chitosan-glucan complexes proceeds from biological sources which are essentially chitin-containing microorganisms. The latter are treated with solutions, the process according to the invention being characterized in that said chitin-containing microorganisms are treated at least once with a first alkaline solution. Then, the product obtained from this step a) is treated with diluted mineral acid. This step b) is followed by a further treatment with a second alkaline solution, the alkalinity of said second alkaline solution being higher than that of said first alkaline solution. The alkalinity of the second alkaline solution is adjusted such that deacetylation of the product obtained from the preceding step does not proceed to completion. This is followed by separating the solid components from this treatment step c), and then discarding the supernatant, neutralizing the residue and washing the residue with water.

The process according to the invention has the advantage that it modifies the fungal mycelia mildly so that the native structure of the cell walls is essentially retained and the degree of deacetylation becomes controllable. This is especially advantageous for adjusting the properties of the materials according to the invention obtainable by the process according to the invention in order to direct them to a wide variety of applications. Thus, for example, a higher acetylation level is desirable if the materials according to the invention are employed in wound healing, for example. However, if the product obtainable by the process according to the invention is to be employed as a sorbent, for example, it may be advantageous to increase the degree of deacetylation to obtain more complexing sites or sorption sites through free amino groups.

In the process according to the invention, there are preferably used chitin-containing microorganisms, such as zygomycetes, ascomycetes, plectomycetes, streptomycetes, pyrenomycetes, discomycetes and/or yeasts. These include, in particular, Aspergillus sp., Penicillium sp., Mucor sp., Phycomyces sp., Choanephora sp., Zygorrhynchus sp., Blakeslia sp., Actinomyces sp. and Saccharomyces sp. Preferably, the microorganisms mentioned are employed in the stage of highest chitin content and/or in the final condition of their application for industrial purposes. Basically, however, the stage of development is not critical. Said fungi or yeasts are characterized by having a chitin content in their cell walls.

According to the invention, it is preferred to perform the treatment with said first alkaline solution according to step a) twice to four times.

The alkalinity of the first alkaline solution is preferably from 1 to 15%, in particular from 5 to 10%. The temperatures are preferably in the range of from 50 to 110° C., in particular from 60 to 900° C.

Preferably, the normality of the mineral acid to be used in step b) is from 0.5 to 5. Hydrochloric acid, nitric acid, ortho-phosphoric acid or combinations thereof may be used as said mineral acid. Sulfuric acid is less preferred since in the treatment with sulfuric acid, a tendency towards the precipitation of sulfates cannot always be prevented.

Preferably, the concentration of the second alkaline solution according to step c) is from 10 to 35%, in particular from 20 to 30%. The treatment temperature is preferably between 90 and 150° C., and the treatment preferably lasts for between 30 and 180 min, in particular between 60 and 120 min, between 60 and 90 min being particularly preferred. According to the invention, aqueous sodium hydroxide or potassium hydroxide are preferably employed. Thus, according to the invention, the chitin-containing mycelia of the molds are treated with a less concentrated alkaline solution prior to deacetylation in order to eliminate, for example, pigments, lipids and proteins. The demineralization is performed with low-concentrated mineral acid, preferably at room temperature. The fungal mycelia thus processed are then deacetylated with the second alkaline solution. From electron-microscopical examinations, it can be seen that the native structure of the cell walls is essentially retained in the process according to the invention. The demineralization required according to the invention in step b) of claim 1 removes salts from the cell walls, preferably after a treatment period of 2 hours at room temperature.

The advantages of the process according to the invention reside in the facts that the chitosan-glucan complexes obtainable thereby have been exposed to a relatively low alkali concentration, that short incubation times can be employed, that improvements of the degree of purity of the complex can be achieved, and that the native structures of the cell wall are retained. Highly effective novel sorbents can thereby be provided which are biologically degradable and non-toxic. Thus, new fields of applications of these materials become available, for example, in medicine, in food industry and in environmental protection.

Thus, another subject-matter of the present invention are materials obtainable by the process according to the invention which essentially consist of a chitosan-glucan complex. "Essentially" as used herein means that small amounts of other substances, in particular chitin or acetyl groups or residual minerals, may also be present in the material. However, the degree of purity is quite high.

The materials according to the invention obtainable by the process according to the invention are especially characterized in that the structure of the cell walls of the microorganisms from which the materials are derived are still essentially intact. The ash content of these materials is below 10%. This is another statement which defines the term "essentially" in a sufficient manner for one skilled in the art.

The materials according to the invention may be influenced in their degree of deacetylation by means of the process according to the invention. Thus, an increased deacetylation can be achieved by extending the time of exposure of the mycelium and an increase of the second alkaline solution, whereas a lower degree of deacetylation can be adjusted with a treatment at a lower concentration of alkali or at a lower temperature within a shorter period of time.

From the materials according to the invention, shaped materials can be prepared, for example, by subjecting a suspension of the material according to the invention to freeze-drying. The shaped materials may especially be in the form of porous films, such as membranes, mats, plasters, fleeces, especially in the form of so-called non-woven fabrics, or threads. The shaped materials may also be formed from a first material consisting of the material according to the invention, and a second material containing cellulose. In particular, such shaped materials may be in the form of a film or a sheet-like structure. In particular, wound-healing means may be prepared from the shaped or unshaped materials according to the invention, preferably in the form of sheets or strips. Applied as plasters to a wound, they may then accelerate the healing of this wound. If the material according to the invention is shaped into threads, the latter can be employed as surgical suture materials.

A further field of application of the materials according to the invention may be as enterosorbents. This term means sorbents capable of binding substances from body fluids, such as blood serum, or in the stomach. These include, for example, cholesterol or other materials which may be present in increased concentrations, e.g., in pathological cases. In a similar way, other body fluid, such as urine, for example, can be purified with these sorbents. In particular, due to the sorptive power, bacteria and toxins, undesirable enzymes etc can be bound. The application as a wound cover also relies on the sorptive power of the materials according to the invention, which results in tissue dehydration, for instance. An advantageous effect especially results from the action of hydrolyzing enzymes, such as lysozyme, on the materials according to the invention. This yields oligosaccharides which may have a healing activity, such as oligomers consisting of or comprising N-acetylglucanamine, for example. Thus, it may be useful in such cases to keep the degree of deacetylation as low as possible in order to ensure a high level of release of the desired oligosaccharides. Due to its sorptive character, the material according to the invention may have a bacteriostatic or even bactericidal effect by adsorbing bacteria. This is especially advantageous in the use of the materials according to the invention as a wound cover or enterosorbent. Due to this bactericidal property, the materials according to the invention may also be useful as stabilizers for foods, especially emulsions.

The materials according to the invention in a shaped form, for example, as membranes or molded parts, as well as in a packed form are useful for removing and/or recovering substances, especially from solutions. The substances to be sorbed may be both organic and inorganic substances. Thus, for example, heavy metals can be removed from aqueous solutions, so that the materials according to the invention can be employed in environmental protection. Organic substances, especially pesticides, herbicides and other harmful organic substances, can also be removed from solutions. In this field of application too, the materials according to the invention can be useful in environmental protection.

Another interesting application is the use as a chromatographic auxiliary for the separation or immobilization of biopolymers, such as enzymes, antibodies and catalysts. Thus, adsorption data from transition metal ions show these may also be separated from alkali and alkaline earth elements by means of the complex. For example, if lysozyme is separated on the chitosan-glucan complex by chromatography in a column, it retains 70% of its activity.

In addition, other applications of the materials according to the invention are also possible, for example, in the preparation of products and formulations, such as glues, adhesives-, flocculants, coagulation aids, substrates for enzymes, adsorbants for chromatographical purposes, production agents, paper additives, auxiliaries and additives for textiles, for glass wool, for plastics, for dyes, for natural and artificial skins, for pharmaceutical capsules, for cell aggregation, for microbiological media, for culture media as well as foodstuffs for humans and animals.

Due to the high degree of purity of the prepared chitin-chitosan-glucan complexes, i.e. the low content of protein and melanin and the low content of minerals, especially carbonates (ash content), and the high and/or adjustable degree of deacetylation, and due to the essential conservation of the cell wall structure, defined products having defined properties can be obtained. The outstanding property is, in particular, the high capacity of sorption (see table 4), which is positively influenced by all three treatment steps, of many materials from solutions, such as biological fluids (blood, serum), waste waters etc. for removing, storing and/or reuse. In addition, the product is non-toxic and biologically degradable.

In practice, the relevant properties include the sorptivity, especially for heavy metals including uranium and other radio-nuclides, as well as that for bacteria and their toxins and metabolites, proteins and lipids and other organic and biological compounds, such as cholesterol, urea, pesticides, dioxin, dyes, aldehydes, acids etc.

For different uses, the chitin-chitosan-glucan complex with retained cell wall structure may be prepared, not only as, a powder or granules, but also readily in other forms, such as film, sheet, membrane (self-supporting), paper, "blotting paper" (especially in a composite with cellulose), spongy or web-like structure (by freeze-drying, e.g. plaster). Further applications are as a flocculant for polyelectrolytes and colloids and as stabilizers for emulsions.

A number of possible applications of the product in medicine result from its properties. The high sorption capacity for undesirable materials and the non-toxicity which has been shown in animal experiments result in the applicability as an enterosorbent for the purification of the gastrointestinal tract or the blood as well as the reduction of the concentration of certain substances in blood, such as cholesterol.

The web-like structure permits the preparation of elastic, highly porous, i.e. highly air-permeable, plasters for wound covering. Visible pores can be produced. The porosity can be adjusted by gassing during freeze-drying. By the addition of desirable substances, the plasterwmay serve as a depot for them. The degradation of chitin-chitosan structures by hydrolys is (e.g. with lysozyme) releases oligosaccharides containing N-glucosamine and N-acetylglucosamine units directly on the plaster which participate in tissue regeneration and accelerate wound healing. The cell proliferation is activated, the formation of-epithelium is stimulated, and the formation of collagen phases is reduced (healing of large wounds without scars). Through the sorption of bacteria, the plaster has a "bactericidal" activity. The sorption of inflammation mediators and proteolytic enzymes has also a positive effect.

Due to its high water-absorbing capacity (when dried, the product will lose water to the extent of 500% of its dry weight), the material can be employed for tissue dehydration and wound drainage.

The invention will now be further explained by the following examples.

EXAMPLE 1

Preparation of a Chitosan-Glucan Complex from *A. niger* from Waste of Citric Acid Production 1. Removal of protein and the like: To 150 g of mycelia (wet weight) of *A. niger* in a chemical reactor of 2 l of total volume was added 1.5 l of 8% aqueous sodium hydroxide. The dispersion obtained was stirred at 90° C. for 60 min (60 rpm). Thereafter, the contents were filtered through a fabric filter. The filter cake was stirred once again with 1.5 l of 8% aqueous sodium hydroxide at 90° C. for 60 min. The product obtained was filtered and washed three times with a 20fold excess of water.

2. Removal of minerals (especially carbonate): The product in the reactor was treated with 1.5 l of 2 N hydrochlorid acid at room temperature for 120–180 minutes, then filtered and washed with distilled water to neutrality. 90–95 g (wet weight) of chitosan-glucan complex from *A. niger* mycelia (or 18–19 g of dry weight) was obtained.

3. Deacetylation: The product from 2. was stirred in a reactor with 1.0 l of 29% of aqueous sodium hydroxide at 125° C. for 90 minutes. Then, the material was filtered through glass fabric. To the filter cake was added in a reactor 4 l of distilled water with stirring. In the course of 180–240 minutes, a 4% hydrochloric acid was continuously added to the obtained dispersion until a pH value of 6.5 to 7.0 was reached. The neutralized product was filtered and washed with a tenfold excess of distilled water. 65 g (wet weight) of chitin-chitosan-glucan complex from *A. niger* mycelia (or 17 g of dry weight) was obtained. The product was colorless. Especially in the dispersion, it could be seen that the cell walls had been conserved which was confirmed by electron micrographs. The degree of deacetylation, based-on the chitin in the chitin-glucan complex, was 89%.

EXAMPLES 2 to 11

Preparation of Chitosan-Glucan Complexes from *A. niger* from Waste of Citric Acid Production.

Basically as in Example 1. Table 1 sets forth the different conditions.

Example 10 was prepared in accordance with DE-A-29 23 802 ("prototype").

Example 11 shows a preparation in a pilot plant scale in accordance with No. 1: 6 kg of mycelia with 60 l of 8% aqueous sodium hydroxide in the first step and 60 l of 2 N hydrochlorid acid in the second step yields 4.9 kg of chitin-glucan complex from which 4.5 kg (wet weight) of chitin-glucan complex, corresponding to 0.8 kg of dry weight, is obtained with 50 l of 29% aqueous sodium hydroxide.

According to Examples 1 to 9, chitin-chitosan-glucan complexes were also prepared from mycelia of *P. chrysogenum* (Nos. 12–20), *Blakeslia trispora* (Nos. 21–29), and *Streptomyces sp.* (Nos. 30–38).

Table 2 shows the effect of protein removal and demineralization (carbonate removal). The protein content in the chitin-glucan complex was determined with the Folin reagent at 750 nm (low-concentration range) and 500 nm (high-concentration range). The protein content was determined from a calibration curve with bovine serum albumin standards according to R. M. C. Dawson et al., "Data for Biochemical-Research", Clarendon Press, Oxford 1986, page 550, the melanin content was determined by spectrophotometry according to A. Malama, "Biologically active substances from microorganisms", in Nauka i Technika, Minsk, 1975, pages 120–126.

Table 3 shows the effect of deacetylation. The degree of deacetylation was determined with UV spectroscopy according to R. A. A. Muzzarelli, G. Rochette, "Determination of the Degree of Deacetylation of Chitin by First Derivative UV-Spectrometry" in Carbohydr. Res. 1985, 5, pages 461–472. The stated cation-exchange capacity relates to equilibrium. No. 10 is the "prototype" according to DE 29 23 802.

From the data, it can be seen that the degree of deacetylation increases with reaction time, but also that the disruption of cell walls increases at too high reaction times (depending on the concentration of alkali and temperature). The proportion of the water-soluble fraction of the chitin-chitosan-glucan complex also increases with reaction time.

The chemical shifts in the $^1$H NMR spectrum of the soluble fraction and the titration of amino groups shows it to be chitosan.

Table 4 shows the equilibrium sorption capacities for heavy metal cations, the dyes Active Red and Active Blue, and the protein bovine serum albumin. The sorption experiments were performed with 0.1 g of chitosan-glucan complex in 50 ml of water, wherein heavy metal cations were employed in concentrations of 52 mg/ml (the following salts were used: $Pb(NO_3)_2$, $Hg(Ac)_2$, $K_2Cr_2O_7$ and $CuSO_4$), the quantity of dye was about 70 mg/ml, and the quantity of protein was about 10 mg/ml. The values are clearly above those mentioned in DE 29 23 802 for the chitosan-glucan complex prepared therein (10*, Table 4), which correspond to those which were found for the prototype No. 10 prepared according to the protocol therein.

In addition, the percent decrease of cholesterol concentration from 50 ml solutions with 100 mg/l and 0.1 g of chitosan-glucan complex is given for two complexes.

TABLE 1

Conditions in the Preparation of Different Chitosan-Glucan Complexes from Mycelia of *A. niger*

| | 1. Protein removal | | | 2. Demineralization | | | 3. Deacetylation | | | | | |
|---|---|---|---|---|---|---|---|---|---|---|---|---|
| No. | % NaOH | Time (min) | Temp. (° C.) | Acid | Time (min) | Temp. (° C.) | % NaOH | Time (min) | Temp. (° C.) | recovery (g, dry) | deacetyl. % | Remarks |
| 1 | 8 | 60 | 90 | 2x 2 N HCl | 120–180 | 20 | 29 | 90 | 125 | 17 | 89 | |
| 2 | 8 | 60 | 60 | 4x 2 N HCl | 120–180 | 20 | 29 | 90 | 125 | 18 | 83 | |
| 3 | 8 | 60 | 75 | 4x 2 N HCl | 120–180 | 20 | 29 | 90 | 125 | 17.5 | 85 | |
| 4 | 8 | 60 | 90 | 4x 3% $H_3PO_4$ | 120–180 | 20 | 29 | 90 | 125 | 16 | 89 | |
| 5 | 8 | 60 | 90 | 2x 3% $HNO_3$ | 120–180 | 20 | 29 | 90 | 125 | 16.5 | 89 | |
| 6 | 8 | 60 | 90 | 2x 2 N HCl | 120–180 | 20 | 29 | 60 | 125 | 18.5 | 60 | |
| 7 | 8 | 60 | 90 | 2x 2 N HCl | 120–180 | 20 | 29 | 30 | 125 | 20 | 37 | |
| 8 | 8 | 60 | 90 | 2x 2 N HCl | 120–180 | 20 | 29 | 240 | 125 | 14 | 89 | mycelium partly disrupted |
| 9 | 8 | 60 | 90 | 2x 2 N HCl | 120–180 | 20 | 20 | 90 | 125 | 19 | 60 | |
| 10 | 8 | 60 | 90 | 2x — | — | — | 40 | 360 | 128 | 50* | 80 | prototype, mycelium disrupted |
| 11 | 8 | 60 | 90 | 1x 2 N HCl | 120 | 20 | 29 | 90 | 125 | 800 | 80 | technical quantity |

*due to high ash content

TABLE 2

Protein Content and Mineral Content After Steps 1 and 2 (Mycelia from *A. niger*)

| | 1. Protein removal | | | Protein | Melanin | Ash |
|---|---|---|---|---|---|---|
| No. | Time (min) | Temp. (° C.) | | % | % | % |
| 2* | 60 | 60 | 2x | 6.0 | 2.1 | 30.0 |
| 2 | 60 | 60 | 4x | traces | traces | 28.0 |
| 2 | + demineralization | | | traces | traces | 3.0 |
| 3* | 60 | 75 | 2x | 6.0 | 4.0 | 30.0 |
| 3 | 60 | 75 | 4x | traces | traces | 27.0 |
| 3 | + demineralization | | | traces | traces | 8.0 |
| 1 | 60 | 90 | 2x | traces | traces | 18.0 |
| 1 | + demineralization | | | traces | traces | 3.0 |

TABLE 3

Effect of Deacetylation (Mycelia of *A. niger* and *P. chrysogenum*)

| No. | % NaOH | Time (min) | Temp. (° C.) | Appearance | cation-exchange capacity (mg of $H^+$/g) | degree of deacetylation (%) | solubility in HCl, % |
|---|---|---|---|---|---|---|---|
| 1 | 29 | 90 | 125 | native mycelium | 1.0 | 89.0 | 10.0 |
| 6 | 29 | 60 | 125 | native mycelium | 0.6 | 60.0 | 8.0 |
| 7 | 29 | 30 | 125 | native mycelium | 0.4 | 37.0 | 2.0 |
| 8 | 29 | 240 | 125 | partly disrupted mycelium | 1.0 | 89.0 | 11.0 |
| 9 | 20 | 120 | 125 | native mycelium | 0.6 | 60.0 | 2.0 |
| 10 | 40 | 360 | 128 | totally disrupted mycelium | 0.8 | 80.0 | 15.0 |
| 12 | 29 | 90 | 125 | native mycelium | 1.0 | 89.0 | 10.0 |
| 13 | 29 | 60 | 125 | native mycelium | 0.8 | 61.0 | 5.0 |
| 14 | 29 | 30 | 125 | native mycelium | 0.4 | 37.0 | 2.0 |

TABLE 4

Sorption Capacities of the Products from *A. niger*, *P. chrysogenum*, *B. trispora* and Streptomyces sp.

| | mg/g of dried product | | | | | | % decrease of cholesterol |
|---|---|---|---|---|---|---|---|
| No. | Cu (2+) | Hg (2+) | Pb (2+) | Cr (6+) | Dye | Protein | |
| 1 | 240 | 180 | 160 | 30 | 29 | 1000 | 75 |
| 12 | 230 | 168 | 156 | 35 | 25 | 1000 | 90 |
| 21 | 200 | 101 | 98 | 28 | 29 | 700 | |
| 30 | 180 | 98 | 90 | 30 | 18 | 800 | |
| 10* | 25 | | | | | | |
| 10 | 20 | | 10 | | 5 | 100.0 | |

What is claimed is:

1. A process for preparing chitosan-glucan complexes from biological sources comprising:
   a) reacting chitin-containing microorganisms having a cell structure, as said biological sources, at least once in the presence of a first alkaline solution, thereby, separating chitosan glucan complexes from the microorganisms; followed by
   b) reacting the chitosan-glucan complexes in the presence of diluted mineral acid, thereby, demineralizing the chitosan-glucan complexes; followed by
   c) reacting the chitosan-glucan complexes in the presence of a second alkaline solution, the second alkaline solution having a higher alkalinity than the first alkaline solution, thereby, effecting incomplete deacetylation of said chitosan-glucan complexes; followed by
   d) neutralizing the chitosan-glucan complexes, followed by washing with water, thereby, effecting incompletely deacetylized, demineralized chitosan-glucan complexes, while retaining the cell structure of the chitin-containing microorganisms.

2. The process according to claim 1, characterized in that said chitin-containing microorganisms are zygomycetes, ascomycetes, plectomycetes, streptomycetes, pyrenomycetes, discomycetes, or combinations thereof.

3. The process according to claim 1, characterized in that reacting in the presence of said first alkaline solution is performed two to four times.

4. The process according to claim 1, characterized in that reacting in the presence of said first alkaline solution is performed at a temperature of from 50 to 110° C. with a 1 to 15% alkaline solution.

5. The process according to claim 1, characterized in that reacting in the presence of said first alkaline solution is performed at a temperature of from 50 to 110° C. with a 5 to 10% alkaline solution.

6. The process according to claim 1, characterized in that said mineral acid has a normality of 0.5 to 5.

7. The process according to claim 1, characterized in that said mineral acid is hydrochloric acid, nitric acid, orthophosphoric acid, or combinations thereof.

8. The process according to claim 1, characterized in that said second alkaline solution has a concentration of 10 to 35%.

9. The process according to claim 1, characterized in that said second alkaline solution has a concentration of 20 to 30%.

10. The process according to claim 1, characterized in that said first alkaline solution is an aqueous solution of sodium hydroxide or potassium hydroxide and second alkaline solution is an aqueous solution of sodium hydroxide or potassium hydroxide.

11. The process according to claim 1, characterized in that reacting step c) is performed at a temperature between 90 and 150° C. and for a time between 30 and 180 min.

12. The process according to claim 1, characterized in that reacting step c) is performed at a temperature between 90 and 150° C. and for a time between 60 and 120 min.

13. In a method comprising the steps of
   adding a sorption material to a solution of a substance, whereby, the substance is adsorbed by the sorption material, followed by
   removing the sorption material from the solution, whereby, the substance is isolated from the solution, the improvement wherein the sorption material comprises the chitosan-glucan complexes prepared according to the process of claim 1.

14. The method according to claim 13, wherein the substance is a heavy metal.

15. The method according to claim 13, wherein the substance is a harmful organic substance.

16. The method according to claim 15, wherein the harmful organic substance is a pesticide or herbicide.

17. The method according to claim 13, wherein the solution is a biological solution.

18. The method according to claim 13, wherein the sorption material is an enterosorbent in vivo.

19. A method of healing wounds comprising applying to the wound shaped material comprising chitosan-glucan complexes prepared according to claim 1.

20. The method according to claim 19, wherein the material is in the form of a freeze-dried suspension.

21. The process according to claim 1, characterized in that said chitin-containing microorganisms are yeasts.

* * * * *